Figure 1:
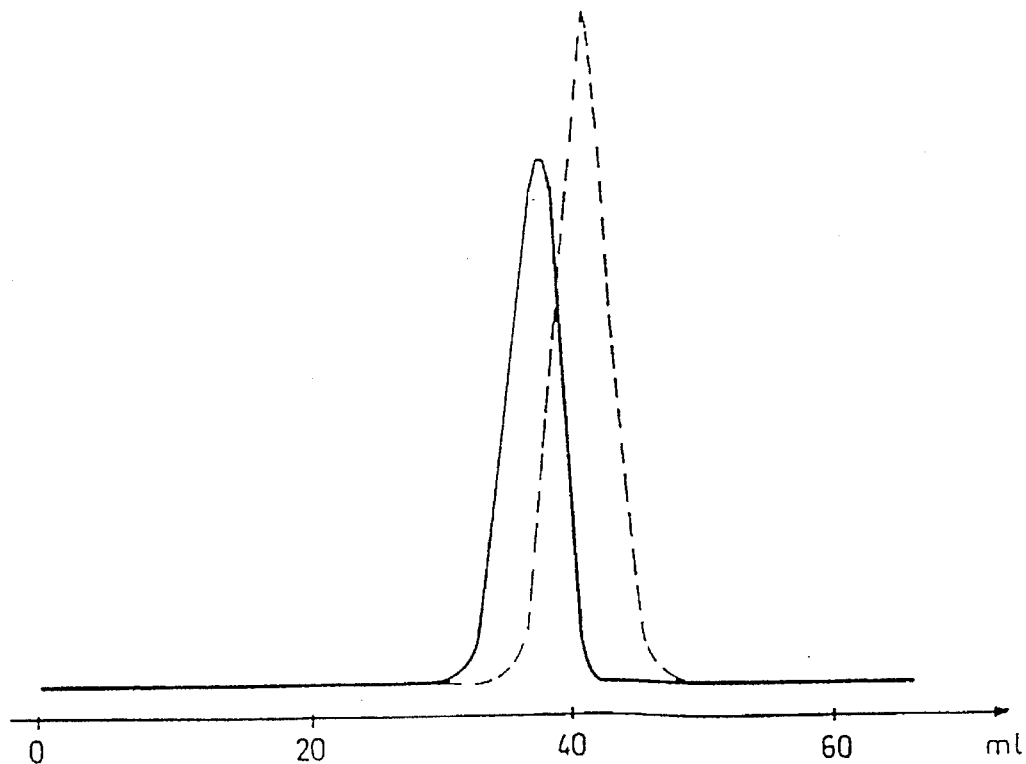

US005514780A

United States Patent [19]
Dellacherie et al.

[11] Patent Number: 5,514,780
[45] Date of Patent: May 7, 1996

[54] DERIVATIVES OF HUMAN HAEMOGLOBIN, METHOD FOR PREPARING THEM, PRODUCTS DERIVED THEREFROM AND USE OF THESE DERIVATIVES AND PRODUCTS

[75] Inventors: Edith Dellacherie, Malzeville; Daniel Sacco, Nancy; Michel Grandgeorge, Vaugneray, all of France

[73] Assignee: Pasteur Merieux Serums et Vaccins, Lyon, France

[21] Appl. No.: 926,673

[22] Filed: Aug. 10, 1992

[30] Foreign Application Priority Data

Aug. 14, 1991 [FR] France ................... 91 10342

[51] Int. Cl.$^6$ .................. C07K 14/805; A61K 38/42
[52] U.S. Cl. ............................... 530/385; 530/399
[58] Field of Search ................... 530/399, 385; 514/2, 12, 21

[56] References Cited

U.S. PATENT DOCUMENTS

| 5,079,337 | 1/1992 | Leonard et al. | 530/385 |
| 5,110,909 | 5/1992 | Dellacherie et al. | 530/385 |
| 5,349,054 | 9/1994 | Bonaventura et al. | 530/385 |

OTHER PUBLICATIONS

Banerjee, R. and Allan Desbois, "Effet des avions polycarboxylate sur l'benioqohine" C. R. Acad Sci. Paris, t. 277 (17 Sep. 1973).

Desbois, A. and R. Banerjee "Effects of Polyvalent Anion Binding to Hemoglobin on Oxygen and Oxidation–Reduction Equilibria and their Relevance to Allosteric Transition" J. Mol. Biol., (1975) 92, 479–493.

Dellacherie, E. and M. Leonard, "Improvement of Oxygen–Carrying Properties of Human Hemoglobin by Chemical Modification with a Benzene Hexacarboxylate–Monosubstituted Polyoxyethylene", Journal of Protein Protein Chemistry, vol. 10, No. 1, 1991, 61–67.

Labrude, P., B. Teisseire and C. Vigneron, "Attempts to use carbodiimide (EDCI) to cross–link hemoglobin for transfusions", Faculte des Sciences Pharmaceutiques et Biologiques, 26 Jul. 1978.

Estep, T. N.; E. W. Bobka; A. A. Ebeling; T. T. Hai; D. J. Nelson; R. J. Pankau, and A. Smak, "Novel Aspects of Diaspirin Cross–Linked Hemoglobin Synthesis and Purification", International Symposium on Red Cell Red Cell Substitutes: Design and Clinical Applications, San Francisco, CA May 16–19, 1989, p. 21.

Bucci, E.; C. Fronticelli; A. Razynska; and B. Urbaitis, "Overview of Chemically Obtained Oxygen Carriers From Hemoglobin: Pseudocrosslinked Tetramers", International Symposium on Red Cell Substitutes: Design and Clinical Applications, San Francisco, CA, May 16–19, 1989, p. 22.

Primary Examiner—Christina Y. Chan
Assistant Examiner—P. Lynn Touzeau
Attorney, Agent, or Firm—Larson and Taylor

[57] ABSTRACT

The invention relates, as new compounds, to derivatives of tetrameric human haemoglobin corresponding to the covalent coupling of a haemoglobin tetramer and a polycarboxy-substituted compound having at least 4 -COO$^-$ groups, the said polycarboxy-substituted compound effecting an internal crosslinking of the two dimers of haemoglobin and conferring thereon an affinity for oxygen which is compatible with an in vivo use of the conjugate when the natural allosteric effector of haemoglobin is not present. Among carboxy-substituted compounds, special mention is made of benzenehexacarboxylate and benzenetetracarboxylate.

14 Claims, 2 Drawing Sheets

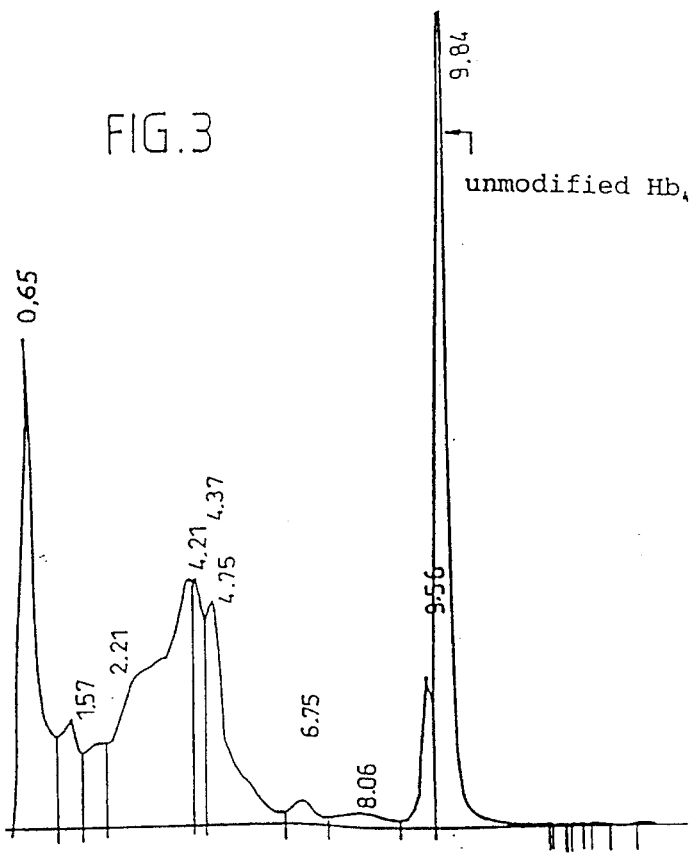
FIG.3
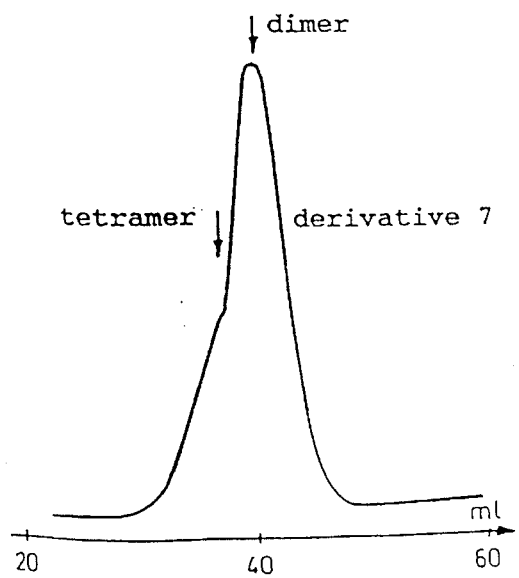
FIG.4
FIG.5

DERIVATIVES OF HUMAN HAEMOGLOBIN, METHOD FOR PREPARING THEM, PRODUCTS DERIVED THEREFROM AND USE OF THESE DERIVATIVES AND PRODUCTS

STATE OF THE ART

The invention relates to new derivatives of human haemoglobin exhibiting good intravascular persistence and an affinity for oxygen which is lower than that of free haemoglobin and which is, more specifically, compatible with an in vivo use for oxygen transport in the absence of the natural allosteric effector of haemoglobin (2,3-diphosphoglycerate, DPG).

The invention also relates to a method for preparing these derivatives, the products derived therefrom and the use of these derivatives and products as oxygen carriers, in particular in the context of transfusions.

From French Patent Applications Nos. 2,600,894 and 2,630,329, it was shown that water-soluble polymers bearing polyanionic sites, and especially polycarboxylate sites, such as, for example, benzenecarboxylate sites, could be linked covalently to human haemoglobin in the presence of a water-soluble carbodiimide and that, even when the reaction was performed with the oxy form of haemoglobin, the resulting conjugates had a much lower affinity for oxygen than the native protein (in the absence of DPG).

While studying, more especially, a conjugate resulting from the binding to oxyhaemoglobin of polyoxyethylene monosubstituted with a site derived from benzenehexacarboxylate, it was demonstrated that the allosteric pocket of the protein—and especially the α-amino function of the β N-terminal valine located in this pocket—was a favoured site for the binding of the polymer (E. DELLACHERIE and M. LEONARD, J. Protein Chem. 1991, vol. 10, No. 1, 61–67). The presence of anionic groups in the vicinity of the allosteric site of haemoglobin confers on the latter a low affinity for oxygen; since its molecular size is increased by the presence of the polymer, the modified haemoglobin also possesses in vivo an increased intravascular persistence compared to the native form (greatly decreased diffusibility through biological membranes).

The use of these polymer conjugates has four major drawbacks, namely the risk of anaphylactic shock (observed with dextrans) associated with their repeated use, problems of intolerance associated with the high molecular weights (formation of multi-tetramers), the viscosity of the solutions containing these conjugates which, in particular, limits tissue penetration, and the cost of the polymers.

Another reaction which has been proposed is that between, on the one hand oxyhaemoglobin, and on the other hand 3,5-dibromosalicylic acid esterified with carboxylic acids such as fumaric acid (T. N. Estep et al. and E. Bucci et al., International Symposium on Red Cell Substitutes, Holiday Inn, Fisherman's Wharf, San Francisco, Calif., USA, 16–19th May 1989—Abstracts).

A. Desbois et al. had studied, in J. Mol. Biol. 1975, 92 (3), 479–493, the action of polycarboxylates having from 2 to 6 carboxylate groups on the behaviour of haemoglobin with respect to oxygen. No covalent bonding was involved, simply an interaction between the polycarboxylate and the haemoglobin.

The Applicant found, most surprisingly, that, under some reaction conditions, the binding of free benzenepolycarboxylic acids, and preferably -tetra to -hexacarboxylic acids, to oxyhaemoglobin gave rise to haemoglobin derivatives possessing an affinity for oxygen which is compatible with an in vivo use when the natural effector is not present and which are incapable of dissociating into dimers. The latter feature provides a novel solution to the problem of vascular and renal leakage of haemoglobin, which makes it possible to dispense with the polymers used hitherto and to avoid crosslinking with poorly controlled agents.

The Applicant found, in addition, that this teaching could be extended to small polycarboxy-substituted molecules having at least 4 -COO⁻ groups. In effect, it became apparent, surprisingly, that these molecules could produce an intramolecular bridge between the two αβ dimers of haemoglobin, thereby effecting an internal crosslinking of the protein. This bridge involves two covalent bonds, so that it is necessary to have at least a further 2 carboxylate groups in order to provide for a sufficient effector role.

THE OBJECT OF THE INVENTION

The subject of the invention is hence a derivative of tetrameric human haemoglobin originating from the covalent coupling of a haemoglobin tetramer and a polycarboxy-substituted compound having at least 4 -COO⁻ groups, the said polycarboxy-substituted compound effecting an internal crosslinking of the two dimers of haemoglobin and conferring thereon an affinity for oxygen which is compatible with an in vivo use of the conjugate when the natural allosteric effector of haemoglobin is not present, that is to say being capable of binding oxygen in a reversible manner which will permit release of the oxygen in the irrigated tissues. The covalent coupling may be carried out equally well in the presence or absence of oxygen, on oxy- or deoxyhaemoglobin.

Preferably, the polycarboxy-substituted molecules possess from 4 to 6 -COO⁻ groups and are advantageously saturated or unsaturated monocyclic molecules or branched or unbranched linear molecules having 4 to 6 carbon atoms in the principal chain.

Preferred molecules can be polycarboxy-substituted benzenes, in particular hexa- or tetracarboxy-substituted benzenes, or alternatively a polycarboxy-substituted cyclohexane.

The subject of the invention is also an oxygen transport solution based on tetrameric human haemoglobin, in which the haemoglobin consists at least partially of a derivative according to the invention.

A further subject of the invention is a method for preparing a tetrameric haemoglobin derivative, in which covalent coupling of the tetrameric haemoglobin molecule, preferably in the form of oxyhaemoglobin, and a polycarboxy-substituted compound as defined above is performed under conditions effecting crosslinking of two dimers of the haemoglobin molecule. This coupling is preferably performed in the presence of an agent that promotes covalent bonding, such as N'-ethyl-N-(3-dimethylaminopropyl)carbodiimide hydrochloride (EDCI) or any other reagent traditionally used in peptide synthesis.

Preferably, the coupling is performed under conditions which provide for a crosslinking yield of at least approximately 50%, and in particular not less than approximately 80%, and a $P_{50}$ of the derivative of not less than 1000 Pa, and in particular not less than 1300 Pa (the $P_{50}$ values being measured in 0.05M Tris buffer, pH 7.2, and at 25° C.).

In the case of benzenehexacarboxylate (BHC), the covalent coupling with haemoglobin may be performed with BHC/Hb and EDCI/Hb mole ratios of 3 and 8 or 5 and 6 approximately, respectively. In the case of benzenetetracarboxylate (BTC), the BTC/Hb and EDCI/Hb mole ratios can be 5 and 32 approximately, respectively.

According to an advantageous feature of the invention, the coupling may be performed in the presence of NaCl.

A further subject of the invention is a stabilised tetrameric haemoglobin solution obtained by this method, and preferably comprising more than 50%, and advantageously more than 80%, of haemoglobin derivative having a $P_{50}$ of not less than 1000 Pa, and preferably not less than 1300 Pa.

The modified haemoglobin tetramers according to the invention have considerable potential in human therapy as oxygen carriers in all cases in which it is desired to improve the delivery of oxygen to the tissues or to the body, for example in cases of severe haemorrhage (as a blood substitute) or of various types of vascular resistance (as oxygen carriers smaller in size than red cells) or alternatively, for example, in cases of angioplasty necessitating a shunt with the use of a blood substitute.

The subject of the invention is hence also the use of derivatives or solutions according to the invention for the manufacture of a preparation for oxygen transport in man.

The invention will now be described in greater detail in relation to FIGS. 1 to 5, using examples applied to the covalent coupling to haemoglobin of benzenehexacarboxylate (BHC) and benzenetetracarboxylate (BTC), in the presence of N'-ethyl-N-(3-dimethylaminopropyl)carbodiimide hydrochloride (EDCI).

A BRIEF DESCRIPTION OF THE FIGURES

FIG. 1 shows the dissociation of native haemoglobin into dimers, demonstrated by size exclusion chromatography on Sephacryl S-100 gel. The peak in a continuous line corresponds to the tetramer (0.05M phosphate buffer), and the peak in a broken line, which occurs in a retarded position relative to the tetramer, corresponds to the dimers (in 1M $MgCl_2$); detection at 254 nm.

Figure 2:
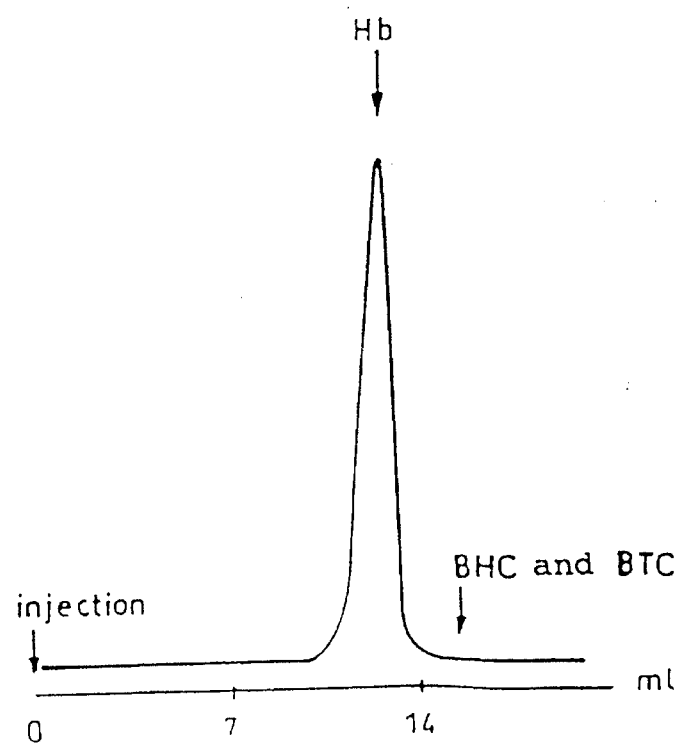

FIG. 2 gives the typical profile (chromatogram) obtained by gel filtration (on TSK G4000 SW) in phosphate medium for the different haemoglobin derivatives obtained according to the invention. The arrows indicate the normal elution volumes of native haemoglobin and of the benzenepolycarboxylic acids (BHC and BTC); detection at 254 nm.

FIG. 3 gives the elution profile of the derivative 4 (Example 4, Table I) on a Mono S cation exchange column; detection at 415 nm.

FIGS. 4 and 5 give the profiles of the products obtained in Examples 4 (Table I) and 7 (Table II), obtained by filtration on Sephacryl S-100 gel in an $MgCl_2$ medium; detection at 254 nm.

EXAMPLES

The techniques of analysis of the haemoglobin derivatives given as examples are as follows:

1) Size exclusion chromatography on a TSK G4000 SW column (30 cm) (Touzart and Matignon—France) in 0.05M phosphate buffer, pH 7.2, at 0.7 ml/min, to monitor, on the one hand the size of the modified haemoglobin (checking especially for the absence of intermolecular crosslinking), and on the other hand the absence of residual benzenepolycarboxylic acid.

2) Ion exchange chromatography on a Mono S column (25 cm) (Pharmacia—Sweden) in 10 mM malonate buffer at pH 5.7 with an LiCl gradient from 0 to 0.3M, to evaluate the level of unmodified haemoglobin tetramers (flow rate 2.5 ml/min).

3) Size exclusion chromatography on Sephacryl S-100 gel (1.6×40 cm) in 0.1% Tris buffer, pH 7.0, 1M $MgCl_2$, at 50 ml/h, to evaluate the level of dissociation of the modified haemoglobin into dimers. In effect, under these conditions, native haemoglobin is completely dissociated into $\alpha\beta$ dimers, as shown in FIG. 1.

4) Measurement of the $P_{50}$ (partial pressure of oxygen for which 50% of the haemoglobin is oxygenated) in 0.05M Tris buffer, pH 7.2, and at 25° C.

Examples 1 to 5 (Table I)

5.5 ml (Examples 1, 2 and 4) or 9.25 ml (Examples 3 and 5) of an aqueous solution of BHC of concentration 7.8 mM, brought beforehand to pH 5.8 with 0.1M sodium hydroxide, are added to 10 ml of a solution of naturally oxygenated human haemoglobin of concentration 1.4mM. The pH of this mixture is adjusted to 6.5 using 0.1M HCl and the mixture is made to a final volume of 30 ml with distilled water.

11 mg (Example 1), 16.5 mg (Examples 2 and 3) or 22 mg (Examples 4 and 5) of EDCI are then added with stirring. The reaction is continued for 2 h at 20° C. The derivatives (crosslinked haemoglobin) 1 to 5 are thereby obtained.

Example 6 (Table I)

The procedure is as in the above examples, with 10 ml of haemoglobin solution (1.4 mM), 5.5 ml of a solution of BHC (7.8 mM) at pH 5.8 in 0.1M NaCl, and 22 mg of EDCI.

The pH of the solution is adjusted to 6.5 with 0.1M HCl and the mixture is made to a final volume of 30 ml with an NaCl solution so as to have a final concentration of 0.1M. The derivative (crosslinked haemoglobin) 6 is obtained.

Examples 7 to 9 (Table II)

4.7 ml, 9.4 ml and 18.8 ml, respectively, of an aqueous solution of BTC of concentration 15 mM, brought beforehand to pH 5.8 with 0.1M sodium hydroxide, are added to 10 ml of an oxyhaemoglobin solution of concentration 1.4 mM. The pH of this mixture is adjusted to 6.5 with 0.1M HCl and the mixture is made to a final volume of 30 ml with distilled water.

22, 44 and 88 mg, respectively, of EDCI are then added with stirring, and reaction is allowed to continue for 2 h at 20° C. The derivatives (crosslinked haemoglobin) 7, 8 and 9 are thereby obtained.

Examples 10 to 12 (Table II)

Identical to Examples 7 to 9, except for, respectively, 18.8 ml, 4.7 ml and 4.7 ml of BTC solution and 66, 44 and 88 mg of EDCI. The derivatives (crosslinked haemoglobin) 10, 11 and 12 are thereby obtained.

TABLE I

Haemoglobin (Hb) - BHC coupling

| Example | BHC/Hb mole ratio | EDCI/Hb mole ratio | Unmodified Hb$_4$ % (a) | Total modified Hb$_4$ (e) % | Crosslinked Hb$_4$ % (b) | $P_{50}$ Pa (c) |
|---|---|---|---|---|---|---|
| 1 | 3 | 4 | 48 | 52 | 7 | 2120 |
| 2 | 3 | 6 | 44 | 56 | ~50 | 1970 |
| 3 | 5 | 6 | 15 | 85 | 25 | 1210 |
| 4 | 3 | 8 | 20 | 80 | 80 | 1200 |
| 5 | 5 | 8 | 9 | 91 | 80 | 870 |
| 6(d) | 3 | 8 | 12 | 88 | 68 | 2270 |

TABLE II

Haemoglobin (Hb) - BTC coupling

| Example | BTC/Hb mole ratio | EDCI/Hb mole ratio | Unmodified Hb$_4$ % (a) | Total modified Hb$_4$ (e) % | Crosslinked Hb$_4$ % (b) | $P_{50}$ Pa (c) |
|---|---|---|---|---|---|---|
| 7 | 5 | 8 | 17 | 83 | 13 | 2025 |
| 8 | 10 | 16 | 14 | 86 | 20 | 1865 |
| 9 | 20 | 32 | 10 | 90 | 18 | 930 |
| 10 | 20 | 24 | 18 | 82 | 8.5 | 1500 |
| 11 | 5 | 16 | 3 | 97 | 28 | 1970 |
| 12 | 5 | 32 | 3 | 97 | 61 | 1000 |

Legends to the tables:
(a) Percentage determined from the chromatograms on Mono S (cation exchange).
(b) Percentage determined from the chromatograms on Sephacryl S-100 in a 1M MgCl$_2$ medium.
(c) In 0.05M Tris buffer, pH 7.2, 25° C.; the $P_{50}$ of native haemoglobin under the same conditions is 500 Pa, and in the presence of DPG, the $P_{50}$ max is 1330 Pa.
(d) Reaction carried out in the presence of 0.1M NaCl.
(e) Includes the crosslinked haemoglobin molecules according to the invention and those to which polycarboxy-substituted molecules have become bound without creating the crosslinking bridge (for example binding outside the protein); (e) = 100 − (a).
Hb$_4$ = haemoglobin in exclusively tetrameric form (even in a dissociating medium such as MgCl$_2$ which is encountered in the chromatographic runs on Sephacryl S-100 - FIG. 4).

The analysis of the examples must take account both of the crosslinking yield and of the $P_{50}$ of each derivative. A suitable solution should preferably contain at least approximately 50% of crosslinked haemoglobin, 80% being considered a very good result, for a derivative having a $P_{50}$ equal to at least 1000.

The disparity of the results obtained for each polycarboxy-substituted benzene shows the importance of the reaction conditions, namely, chiefly, the polycarboxy-substituted molecule/Hb and EDCI/Hb mole ratios (EDCI promotes the creation of covalent bonds) and, where appropriate, the presence of NaCl (Example 6). For each candidate polycarboxy-substituted molecule, it will be easy for a person skilled in the art to determine the optimal conditions.

In the present case, Examples 4, 6 and 12 and, to a lesser extent, Example 2 are very satisfactory.

In FIG. 3, on the basis of Example 4, the multiplicity of species formed after coupling with BHC is observed. These species differ from one another in their acidity (molecules less retarded on the cation exchange column than the unmodified initial tetramer). In this example, the % of unmodified haemoglobin is 20. The stronger or weaker acidity of the modified species depends on the number of acid BHC residues bound to the molecule.

FIGS. 4 and 5 show the profiles obtained by gel filtration in an MgCl$_2$ medium for Examples 4 (80% crosslinking, $P_{50}$=1200) and 7 (13% crosslinking, $P_{50}$=2025). These profiles show very clearly the respective proportions of crosslinked tetramers and dimers (it may be recalled, in effect, that, in an MgCl$_2$ medium, haemoglobin is completely dissociated into dimers, as shown in FIG. 1).

The derivatives 1 to 12 were pooled in order to observe their size distribution, among themselves and relative to native haemoglobin. The chromatogram of FIG. 2 shows a single peak coincident with that of native haemoglobin, thereby showing that, very advantageously, there is no intermolecular crosslinking between haemoglobin molecules. In addition, no peak is observed at the elution volume of BHC and BTC.

Another important advantage of the invention consists in the fact that the method applies to oxyhaemoglobin, thereby affording great ease of handling. Naturally, the same results are obtained with deoxyhaemoglobin.

While in Examples 1 to 12 the covalent coupling was carried out in the presence of EDCI, it remains nonetheless the case that the other coupling methods customarily used in peptide synthesis are also suitable.

We claim:

1. A tetrameric human haemoglobin for delivering oxygen to tissues and to the human body, formed by the covalent coupling of an oxyhaemoglobin tetramer and a polycarboxy-substituted compound, selected from the group consisting of tetracarboxy-substituted compounds and hexacarboxy-substituted compounds, the said polycarboxy-substituted compound being saturated or unsaturated monocylic molecules or branched or unbranched linear molecules having 4 to 6 carbons in the principal chain and effecting an internal crosslinking of the two dimers of haemoglobin and conferring thereon an affinity for oxygen.

2. Haemoglobin according to claim 1, characterised in that the monocyclic molecule is a polycarboxy-substituted benzene.

3. Haemoglobin according to claim 2, characterised in that the polycarboxy-substituted molecule is hexacarboxy-substituted benzene.

4. Haemoglobin according to claim 2, characterised in that the polycarboxy-substituted molecule is tetracarboxy-substituted benzene.

5. Haemoglobin according to claim 1, characterised in that the polycarboxy-substituted molecule is a polycarboxy-substituted cyclohexane.

6. Oxygen transport solution based on tetrameric human haemoglobin, in which the haemoglobin consists at least partially of a haemoglobin according to claim 1.

7. A method for preparing a tetrameric human haemoglobin comprising the step of covalently cross-linking a tetrameric human oxyhaemoglobin in an aqueous solution with a polycarboxy-substituted non-polymeric compound having at least four COO$^-$ groups.

8. Method according to claim 7, characterised in that the crosslinking step is performed in the presence of a coupling agent.

9. Method according to claim 8, characterised in that the said agent is N'-ethyl-N-(3-dimethylaminopropyl)carbodiimide hydrochloride (EDCI).

10. Method according to claim 7, characterised in that the covalent coupling of oxyhaemoglobin and benzenetetracarboxylate (BTC) is performed with BTC/Hb and EDCI/Hb mole ratios of 5 and 32 approximately, respectively.

11. Method according to claim 7, characterised in that the coupling is performed in the presence of NaCl.

12. Stabilised tetrameric haemoglobin solution obtained by the method according to claim 7.

13. Haemoglobin solution according to claim 12, comprising more than 50%, of haemoglobin derivative having a $P_{50}$ between 1000 Pa and 2270 Pa or between 1300 Pa, and 2270 Pa.

14. Method according to claim 7, characterised in that the covalent coupling of oxyhaemoglobin and benzenehexacarboxylate (BHC) is performed with BHC/Hb and EDCI/Hb mole ratios of 3 and 8 or 5 and 6 approximately, respectively.

* * * * *